United States Patent [19]

DeBondt

[11] Patent Number: 4,566,806
[45] Date of Patent: Jan. 28, 1986

[54] METHOD AND DEVICE FOR CONTROLLING THE CURING RATE OF CONCRETE

[76] Inventor: Dick DeBondt, No. 6, De Ruyterstraat, Rujssen, Netherlands

[21] Appl. No.: 504,044

[22] PCT Filed: Oct. 22, 1982

[86] PCT No.: PCT/NL82/00038
§ 371 Date: May 31, 1983
§ 102(e) Date: May 31, 1983

[87] PCT Pub. No.: WO83/01411
PCT Pub. Date: Apr. 28, 1983

[30] Foreign Application Priority Data
Oct. 23, 1981 [NL] Netherlands ............. 8104811

[51] Int. Cl.[4] ............................................. G01N 3/26
[52] U.S. Cl. .......................................... 374/53; 374/45
[58] Field of Search ................ 374/5, 10, 11, 12, 13, 374/16, 19, 20, 25, 53, 45, 50; 264/40.6

[56] References Cited

U.S. PATENT DOCUMENTS 3,649,729 3/1972 Davis et al. ............................ 374/53
3,718,721 2/1973 Gould et al. ........................... 374/53
4,044,600 8/1977 Claxton et al. ....................... 374/53

Primary Examiner—Charles Frankfort
Assistant Examiner—David R. Schuster
Attorney, Agent, or Firm—John P. Snyder

[57] ABSTRACT

A method and device for controlling the curing rate of concrete comprising the measuring of the temperature of the concrete, assessing the momentaneous maturity of the concrete by means of the temperature variation and controlling the heat supply or dissipation on the basis of the momentaneous maturity in a manner such that at the end of the period the concrete has the desired maturity. A preferred embodiment of the device according to the invention comprises a temperature measuring device (15) to be connected to at least one temperature sensor (6,7), and a calculating device (16) connected to the temperature measuring device (15), assessing the momentaneous maturity and provided with a data input member (17) and a display member showing the assessed momentaneous maturity.

8 Claims, 4 Drawing Figures

METHOD AND DEVICE FOR CONTROLLING THE CURING RATE OF CONCRETE

The invention relates to a method of controlling the curing rate of concrete comprising the step of influencing the heat supply or dissipation for a given period of time.

In the concrete building industry, for example, it is common practice to set up the casing for part of a building during the day, to pour the concrete and to mount the heating device. During the 16 hours between the end of the workday and the start of the next the fresh concrete is heated so that at the beginning of the next workday it is sufficiently strong to permit of removing the casing. This casing can be set up again the same day for pouring the concrete of a further part of the building. By heating the concrete the curing time of many days in a natural process can be reduced to 16 hours between two workdays. In order to assess whether the concrete is, indeed, sufficiently strong to allow removal of the casing, test cubes are made simultaneously with the building part and also subjected to the thermal treatment. At the beginning of the workday the strength of said test cubes is checked and if it is found sufficient, the casing can be removed. If it is found that the strength of the test cubes is not sufficient, the casing cannot be removed so that it is no longer possible to set up this casing again the same day for a next building part. In this case a whole workday is lost.

It is assumed, of course, that the strength of the test cubes is, with reasonable accuracy, representative, of that of the concrete in the casing. However, it has been found in practice that said accuracy is poor. It may, therefore, occur that the casing is removed whereas this would not be allowed for reasons of strength of the concrete and otherwise that costly workdays get lost by not removing the casing where removal were allowed without hazards.

The object of the invention is to provide a method of the kind set forth in the preamble, which does not exhibit these disadvantages. For this purpose the method embodying the invention comprises the steps of measuring the temperature of the concrete, assessing the momentaneous maturity of the concrete by means of the temperature course and controlling the heat supply or dissipation on the basis of the momentaneous maturity in a manner such that at the end of the period the concrete has the desired maturity. The maturity of concrete is characterized as the integral of an exponential function of the concrete temperature with time. In this function a constant depending on the kind of concrete plays an important part. There has been shown a relationship between the relative strength of the concrete and the maturity, wherein the relative strength is the ratio between the strength at a given instant and the strength attained under standard conditions i.e. after 28 days at 20° C. In a given kind of concrete a given relative strength is associated with a given maturity. By regulating the maturity in accordance with the invention by means of temperature-control, it can be ensured that after a given period the concrete has attained a given maturity and hence a given relative strength.

Although in the foregoing reference is made to acceleration of curing of concrete by raising the temperature, the invention may also be applied for decelerating the curing process by temperature reduction.

In the method according to the invention the concrete temperature is preferably measured at a plurality of areas, whilst the heat supply or dissipation is controlled on the basis of a given, momentaneous extreme maturity at the measured temperature. With accelerated curing this extreme maturity will be the lowest given maturity and with decelerated curing this extreme maturity will be the highest assessed maturity. In this way it is ensured that after a given period each part of the concrete has obtained the desired properties.

A simple, but reliable operation is obtained when in accordance with the invention the control is an on/off control on the basis of the temperature variation of the introduced heat after cutting off the heat supply or dissipation. The increase in maturity after cut-off of the heat supply or dissipation is estimated. When the real temperature variation differs from the expected temperature variation intervention is possible by switching on the heat supply or dissipation.

The invention also relates to and provides a device for carrying out the method embodying the invention. This device comprises at least one temperature sensor, for example, a thermocouple to be housed in the concrete, a temperature measuring device to be connected to the temperature sensor and a control-device connected to a data input member to the temperature measuring device and to a heat supply or dissipation device. The data of the concrete, more particularly the relationship between the maturity and the relative strength are introduced into the control-device by the data input member.

The invention furthermore relates to and provides a device for displaying the momentaneous maturity of the concrete comprising a temperature measuring device to be connected to at least one temperature sensor, and a calculating member connected to the temperature measuring device, assessing the momentaneous maturity and provided with a data input member and a display member showing the assessed momentaneous maturity. The method embodying the invention can thus be carried into effect by manually adjusting a heating device or the like in accordance with the maturity displayed at a given instant. This device also permits of checking the curing process in the case of a natural cure.

The device preferably comprises furthermore a display member for the momentaneous strength.

In the following description the invention will be explained more fully with reference to the Figures.

Figure 1:
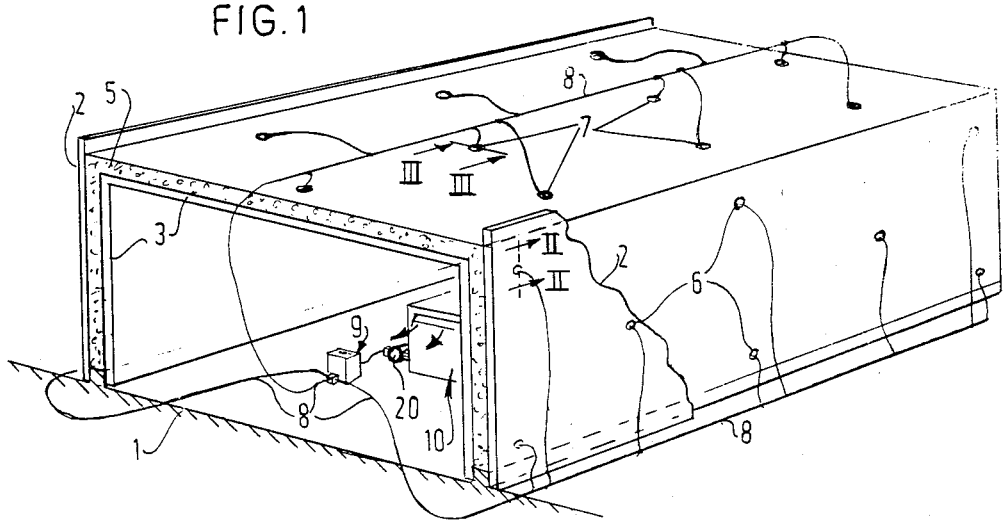
FIG. 1 is a schematic, perspective view of a device under conditions of use, some parts being broken away.
Figure 3:
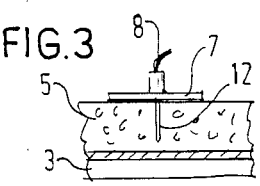
FIG. 3 is a sectional view taken in the direction of the arrow III—III in FIG. 1.
Figure 2:
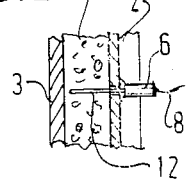
FIG. 2 is a sectional view taken in the direction of the arrow II—II in FIG. 1.
Figure 4:
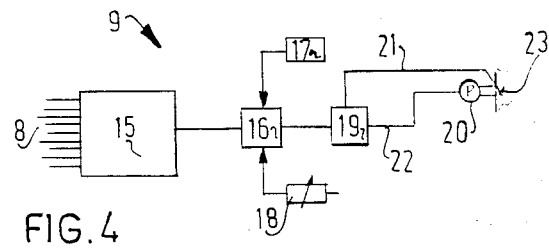
FIG. 4 is a block diagram of the device of FIG. 1.

In a building 1 rising walls and a floor lying thereon are formed by a cast construction method. The rising walls and the floor are made of concrete 5 poured between side casings 2 and a tunnel casing 3. Setting up the casings, the arrangement of the reinforcements (not shown) and pouring the concrete are performed in a single workday. Inside the tunnel casing 3 a heating device 10 is arranged for heating the poured concrete 5 for the period from the end of the workday to the beginning of the next workday so that the curing of the concrete is accelerated. Through the side casings 2 are passed temperature sensors 6, which assess the temperature of the cast concrete 5 by means of a measuring pin 12. The top surface of the cast concrete 5 is also provided with temperature sensors 7, for example, lying on the concrete 5. The temperature sensors 7 assess the temperature of the concrete also with the aid of a measuring pin 12. The temperature sensors 6, 7 are connected through leads 8 to the temperature measuring device 15 of the control-device 9. The temperature measuring device 15 passes a number of temperature values to a control-device 16. To the control-device 16 are furthermore connected a data input member 17 and an adjusting member 18 for the maximum temperature. The adjusting member may be connected to a temperature sensor which assesses the temperature in the space accommodating the heater 10. Thus this space temperature and hence the temperature of the surface of the concrete being in contact with the casing can be prevented from becoming too high. The control-device 16 may comprise a microprocessor which is programmed in a manner such that it controls the heat regulator 19 by means of the data from the temperature measuring device 15, the data input member 17 and the adjusting member 18 for the maximum temperature. By means of the data input member the relationship between the maturity and the relative strength of the concrete used can then be introduced. A further possibility is that only data about the composition of the concrete need be introduced, in which case the control-device 16 calculates the associated relationship between maturity and relative strength and thereby controls the heat regulator 19. The heat regulator 19 controls the burner pump 20 through a lead 22, whilst a monitor 23 is coupled through a lead 21 with the heat regulator 19.

The control-device 16 may be programmed so that it switches on the heater after a given initial period in which the concrete solidifies. After the concrete has reached the set temperature, the heat supply is controlled so that this temperature is maintained. Subsequently, when a given maturity is obtained, the heater is switched off. This assessed maturity corresponds with the desired maturity at the end of the overall period minus the increase in maturity that can be expected after the cut-off of the heat supply up to the end of the period. This increase is calculated by the control-device with the aid of data introduced and relating to the expected temperature drop after the heat supply is switched off. During the cooling period the control-device continues comaring the real temeperature variation with the expected temperature variation. If it appears that the temperature decreases excessively, for example, due to a change of weather conditions, the control-device 16 will again switch on the heater, after which the control-process described above is repeated.

As stated above, the method and device embodying the invention may be employed, not only in the accelerated curing process described above, but also in a decelerated curing process. Decelerated hardening may be desired for obtaining given properties of the material. Decelerated hardening is obtained by keeping the concrete temperature low with the aid of heat dissipation.

The method and device embodying the invention provide an optimum heating process or heat dissipation and thus reduce energy consumption as compared with the methods hitherto known.

The method is described in the foregoing with reference to its application in a cast concrete building process. Apart from this application many other uses are conceivable, for example, in industrial manufacture of concrete elements, prefabricated building parts and the like. Where it is desired to influence a curing process this method can be applied.

I claim:

1. A method of curing concrete to a desired value of cure accumulated over a specified period of time subsequent to pouring thereof, which desired value of cure would not be accumulated over said specified period of time under normal conditions, which comprises the steps of:
   (a) controlling the temperature of the concrete over an initial period of time while the concrete progressively cures to an assessed degree of partial cure thereof which, when augmented by that additional curing calculated to occur by the end of said specified period of time on the basis of an expected temperature variation of the concrete in the absence of such control, will yield said desired value of cure; and
   (b) monitoring further progressive curing of the concrete after said initial period of time and in the absence of said control by measuring temperature variation of the concrete and comparing it with said expected temperature variation to detect disparity between said further progressive curing and said additional curing as calculated, and further controlling the temperature of said concrete when such disparity is detected as would otherwise cause the concrete to accumulate a further progressive curing significantly different from said additional curing as calculated.

2. The method as defined in claim 1 wherein step (a) comprises controlling the temperature of the concrete by first bringing it to a set temperature and then maintaining said set temperature.

3. The method as defined in claim 1 including the step of monitoring the temperature of the concrete during step (a).

4. The method as defined in claim 3 wherein the degree of partial cure of step (a) is assessed on the basis of the temperature of the concrete during step (a).

5. The method as defined in claim 2 including the step of monitoring the temperature of the concrete during step (a).

6. The method as defined in claim 5 wherein the degree of partial cure of step (a) is assessed on the basis of the temperature of the concrete during step (a).

7. A system for imparting a desired maturity to concrete by the end of a predetermined time, which comprises:
   (a) temperature control means for controlling the temperature of the concrete;
   (b) sensing means for sensing the temperature of the concrete; and
   (c) calculating means for calculating the moment at which the concrete has reached a partial value of cure due to the temperature at which the concrete has been kept by said temperature control means which for an expected temperature variation over the remainder of time from said moment to the end of said predetermined time is calculated to provide an additive curing to yield said desired maturity with said temperature control means inactivated, for inactivating said temperature control means at said moment, for monitoring the temperature variation of the concrete during said remainder of time and comparing such temperature variation with said expected temperature variation to determine departure therefrom, and for reactivating said temperature control means in response to departure from said expected temperature variation that would otherwise cause the concrete to accumulate an additive curing significantly different from said additive curing as calculated.

8. A system as defined in claim 7 wherein said temperature control means comprises a heat supply, said sensing means comprises at least one temperature sensor to be housed in the concrete and a temperature measuring device to be connected to said temperature sensor, and said calculating means comprises a control device connected to a data input member, said control device being further connected to said temperature measuring device and said heat supply or dissipation device.

* * * * *